US012788446B2

(12) United States Patent
Biedermann et al.

(10) Patent No.: US 12,788,446 B2
(45) Date of Patent: Nov. 10, 2026

(54) POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/556,328

(22) Filed: Mar. 4, 2026

(65) Prior Publication Data

US 2026/0191566 A1 Jul. 9, 2026

Related U.S. Application Data

(63) Continuation of application No. 18/631,974, filed on Apr. 10, 2024, now Pat. No. 12,599,415, which is a (Continued)

(30) Foreign Application Priority Data

Jul. 18, 2012 (EP) .................................... 12176959

(51) Int. Cl.
*A61B 17/70* (2006.01)
*A61B 17/68* (2006.01)

(52) U.S. Cl.
CPC ...... *A61B 17/7037* (2013.01); *A61B 17/7032* (2013.01); *A61B 17/7035* (2013.01); *A61B 2017/681* (2013.01)

(58) Field of Classification Search
None
See application file for complete search history.

(56) References Cited

U.S. PATENT DOCUMENTS 5,672,176 A 9/1997 Biedermann et al.
5,716,356 A 2/1998 Biedermann et al.
(Continued)

FOREIGN PATENT DOCUMENTS

CN 101264030 A 9/2008
DE 102005021879 A1 11/2006
(Continued)

OTHER PUBLICATIONS

Extended European Search Report for European Application No. 12176959.0, European Search Report dated Nov. 23, 2012 and mailed Dec. 3, 2012 (6 pgs.).

(Continued)

*Primary Examiner* — Tessa M Matthews
(74) *Attorney, Agent, or Firm* — Womble Bond Dickinson (US) LLP

(57) ABSTRACT

A polyaxial bone anchoring device is provided including
- a bone anchoring element (1) comprising a head (3) and a shank (2);
- a receiving part (4, 4') for receiving a rod (100) for coupling the rod to the bone anchoring element, the receiving part comprising a first end (4*a*), an opposite second end (4*b*) and a central axis (C) extending through the first end and the second end, and
- a channel (9) for receiving the rod and an accommodation space (11) for receiving the head;
- a pressure element (6, 6') arranged in the receiving part and configured to exert pressure onto the head;

wherein the pressure element (6) comprises flexible sections (66*a*, 66*b*) facing away from the head (3), characterized in that the flexible sections (66*a*, 66*b*) comprise a free end portion (69*a*, 69*b*) with respect to the central axis (C) that cooperates with an inclined surface portion (15*a*, 15*b*) of the (Continued)

receiving part (4) such as to hold the pressure element (6) in a position in which it exerts a pre-load onto the head before the head is locked.

22 Claims, 9 Drawing Sheets

Related U.S. Application Data continuation of application No. 17/412,013, filed on Aug. 25, 2021, now Pat. No. 11,963,698, which is a continuation of application No. 16/113,277, filed on Aug. 27, 2018, now Pat. No. 11,129,647, which is a continuation of application No. 14/987,504, filed on Jan. 4, 2016, now Pat. No. 10,076,362, which is a continuation of application No. 13/944,328, filed on Jul. 17, 2013, now Pat. No. 9,241,737.

(60) Provisional application No. 61/789,431, filed on Mar. 15, 2013, provisional application No. 61/673,110, filed on Jul. 18, 2012.

(56) References Cited

U.S. PATENT DOCUMENTS

| | | | |
|---|---|---|---|
| 5,728,098 | A | 3/1998 | Sherman et al. |
| 5,954,725 | A | 9/1999 | Sherman et al. |
| 6,010,503 | A | 1/2000 | Richelsoph et al. |
| 6,132,434 | A | 10/2000 | Sherman et al. |
| 6,254,602 | B1 | 7/2001 | Justis |
| 6,355,040 | B1 | 3/2002 | Richelsoph et al. |
| 6,454,773 | B1 | 9/2002 | Sherman et al. |
| 6,471,705 | B1 | 10/2002 | Biedermann et al. |
| 6,554,834 | B1 | 4/2003 | Crozet et al. |
| 7,211,086 | B2 | 5/2007 | Biedermann et al. |
| 7,291,151 | B2 | 11/2007 | Alvarez |
| 7,322,981 | B2 | 1/2008 | Jackson |
| 7,604,655 | B2 | 10/2009 | Warnick |
| 7,662,172 | B2 | 2/2010 | Warnick |
| 7,682,377 | B2 | 3/2010 | Konieczynski et al. |
| 7,699,876 | B2 | 4/2010 | Barry et al. |
| 7,828,829 | B2 | 11/2010 | Ensign |
| 7,875,065 | B2 | 1/2011 | Jackson |
| 7,972,364 | B2 | 7/2011 | Biedermann et al. |
| 8,062,340 | B2 | 11/2011 | Berrevoets et al. |
| 8,088,152 | B2 | 1/2012 | Schumacher |
| 8,123,785 | B2 | 2/2012 | Weaver et al. |
| 8,167,910 | B2 | 5/2012 | Nilsson |
| 8,197,517 | B1 | 6/2012 | Lab et al. |
| 8,257,396 | B2 | 9/2012 | Jackson |
| 8,409,255 | B2 | 4/2013 | Richelsoph |
| 8,435,266 | B2 | 5/2013 | Richelsoph |
| 8,518,082 | B2 | 8/2013 | Sicvol et al. |
| 8,882,817 | B2 | 11/2014 | Jones et al. |
| 8,926,671 | B2 | 1/2015 | Biedermann et al. |
| 8,979,898 | B2 | 3/2015 | Ark et al. |
| 8,998,959 | B2 | 4/2015 | Jackson et al. |
| 9,241,737 | B2 | 1/2016 | Biedermann et al. |
| 9,254,150 | B2 | 2/2016 | Biedermann et al. |
| 9,393,049 | B2 | 7/2016 | Jones et al. |
| 9,895,170 | B2 | 2/2018 | Biedermann et al. |
| 2003/0100896 | A1 | 5/2003 | Biedermann et al. |
| 2003/0100904 | A1 | 5/2003 | Biedermann |
| 2003/0125741 | A1 | 7/2003 | Biedermann et al. |
| 2003/0167058 | A1 | 9/2003 | Shluzas |
| 2004/0097933 | A1 | 5/2004 | Lourdel et al. |
| 2004/0193160 | A1 | 9/2004 | Richelsoph |
| 2004/0236330 | A1 | 11/2004 | Purcell et al. |
| 2005/0080420 | A1 | 4/2005 | Farris et al. |
| 2005/0277928 | A1 | 12/2005 | Boschert |
| 2006/0089644 | A1 | 4/2006 | Felix |
| 2006/0149241 | A1 | 7/2006 | Richelsoph et al. |
| 2006/0200131 | A1 | 9/2006 | Chao et al. |
| 2006/0276789 | A1* | 12/2006 | Jackson ................. A61B 17/70 606/301 |
| 2006/0276792 | A1 | 12/2006 | Ensign et al. |
| 2006/0293664 | A1 | 12/2006 | Schumacher |
| 2007/0043378 | A1 | 2/2007 | Kumar et al. |
| 2007/0118123 | A1 | 5/2007 | Strausbaugh et al. |
| 2007/0123862 | A1 | 5/2007 | Warnick |
| 2007/0167949 | A1 | 7/2007 | Altarac et al. |
| 2007/0270842 | A1 | 11/2007 | Bankoski et al. |
| 2007/0288004 | A1 | 12/2007 | Alvarez |
| 2008/0009862 | A1 | 1/2008 | Hoffman |
| 2008/0045953 | A1 | 2/2008 | Garamszegi |
| 2008/0045970 | A1 | 2/2008 | Saidha et al. |
| 2008/0188898 | A1 | 8/2008 | Jackson |
| 2008/0200918 | A1 | 8/2008 | Spitler et al. |
| 2008/0215100 | A1 | 9/2008 | Matthis et al. |
| 2008/0243185 | A1 | 10/2008 | Felix et al. |
| 2008/0294202 | A1 | 11/2008 | Peterson et al. |
| 2009/0069853 | A1 | 3/2009 | Schumacher |
| 2009/0105770 | A1 | 4/2009 | Berrevoets et al. |
| 2009/0163962 | A1 | 6/2009 | Dauster et al. |
| 2009/0216280 | A1 | 8/2009 | Hutchinson |
| 2009/0254125 | A1 | 10/2009 | Predick |
| 2010/0087865 | A1 | 4/2010 | Biedermann et al. |
| 2010/0125302 | A1 | 5/2010 | Hammill, Sr. et al. |
| 2010/0145394 | A1 | 6/2010 | Harvey et al. |
| 2010/0160977 | A1 | 6/2010 | Gephart et al. |
| 2010/0160980 | A1 | 6/2010 | Walsh et al. |
| 2010/0160981 | A1 | 6/2010 | Butler et al. |
| 2010/0198272 | A1 | 8/2010 | Keyer et al. |
| 2010/0234902 | A1 | 9/2010 | Biedermann et al. |
| 2010/0241175 | A1 | 9/2010 | Walker et al. |
| 2010/0298891 | A1 | 11/2010 | Jackson |
| 2011/0098755 | A1 | 4/2011 | Jackson et al. |
| 2011/0152949 | A1 | 6/2011 | Biedermann et al. |
| 2011/0282399 | A1 | 11/2011 | Jackson |
| 2012/0029569 | A1 | 2/2012 | Iott et al. |
| 2012/0035670 | A1 | 2/2012 | Jackson et al. |
| 2012/0041490 | A1 | 2/2012 | Jacob et al. |
| 2012/0078307 | A1 | 3/2012 | Nihalani |
| 2012/0124813 | A1 | 5/2012 | Biedermann et al. |
| 2012/0143266 | A1 | 6/2012 | Jackson et al. |
| 2012/0221057 | A1 | 8/2012 | Zhang et al. |
| 2012/0253408 | A1 | 10/2012 | Timm |
| 2012/0277799 | A1 | 11/2012 | Winslow et al. |
| 2012/0277800 | A1 | 11/2012 | Jackson |
| 2012/0303064 | A1 | 11/2012 | Walker et al. |
| 2013/0018428 | A1 | 1/2013 | Harper et al. |
| 2013/0197586 | A1 | 8/2013 | Matthis et al. |
| 2013/0258006 | A1 | 10/2013 | Kato |
| 2013/0345761 | A1 | 12/2013 | Biedermann et al. |
| 2014/0142634 | A1 | 5/2014 | Schlaepfer et al. |
| 2015/0032162 | A1 | 1/2015 | Biedermann et al. |
| 2016/0038204 | A1 | 2/2016 | Biedermann et al. |
| 2023/0363800 | A1* | 11/2023 | Jackson ............. A61B 17/7037 |

FOREIGN PATENT DOCUMENTS

| | | | |
|---|---|---|---|
| EP | 0221012 | A1 | 5/1987 |
| EP | 0947174 | A2 | 10/1999 |
| EP | 1 323 391 | A2 | 7/2003 |
| EP | 1570794 | A1 | 9/2005 |
| EP | 1743584 | A1 | 1/2007 |
| EP | 2111811 | A1 | 10/2009 |
| EP | 2 221 012 | A1 | 8/2010 |
| EP | 2286748 | A1 | 2/2011 |
| EP | 2 457 527 | A1 | 5/2012 |
| EP | 2687172 | A1 | 1/2014 |
| EP | 2687172 | B1 | 3/2015 |
| JP | 2010-99293 | A | 5/2010 |
| JP | 2010-194309 | A | 9/2010 |
| WO | WO 2006/116437 | A2 | 11/2006 |
| WO | WO 2006/130179 | A2 | 12/2006 |
| WO | WO 2007/025132 | A2 | 3/2007 |
| WO | WO 2008/008511 | A2 | 1/2008 |
| WO | WO 2008/103150 | A1 | 8/2008 |
| WO | WO 2009/015100 | A2 | 1/2009 |

(56) References Cited

FOREIGN PATENT DOCUMENTS

| | | | |
|---|---|---|---|
| WO | WO 2009/038697 | A1 | 3/2009 |
| WO | WO 2012/064360 | A1 | 5/2012 |
| WO | WO 2012/091737 | A1 | 7/2012 |

OTHER PUBLICATIONS

Search of the Austrian Patent Office by Serv.ip, "Ihr Partner für Forschung und Innovation Express-Recherche zum Stand der Technik," dated Aug. 22, 2012, 6 pp.

Extended European Search Report for European Application No. 13176835.0, European Search Report dated Aug. 20, 2013 and mailed Aug. 29, 2013 (6pgs.).

Japanese Office action for Application No. JP 2013-147396, May 10, 2016 (5 pages), and English translation (6 pages).

* cited by examiner

POLYAXIAL BONE ANCHORING DEVICE

CROSS-REFERENCE TO RELATED APPLICATION(S)

This application is a continuation of U.S. patent application Ser. No. 18/631,974, filed Apr. 10, 2024, which is a continuation of U.S. patent application Ser. No. 17/412,013, filed Aug. 25, 2021, now U.S. Pat. No. 11,963,698, which is a continuation of U.S. patent application Ser. No. 16/113,277, filed Aug. 27, 2018, now U.S. Pat. No. 11,129,647, which is a continuation of U.S. patent application Ser. No. 14/987,504, filed Jan. 4, 2016, now U.S. Pat. No. 10,076,362, which is a continuation of U.S. patent application Ser. No. 13/944,328, filed Jul. 17, 2013, now U.S. Pat. No. 9,241,737, which claims priority to and the benefits of U.S. Provisional Patent Application Ser. No. 61/673,110, filed Jul. 18, 2012 and U.S. Provisional Patent Application Ser. No. 61/789,431, filed Mar. 15, 2013, the contents of which are hereby incorporated by reference in their entirety, and claims priority from European Patent Application EP 12 176 959.0, filed Jul. 18, 2012, the contents of which are hereby incorporated by reference in their entirety.

BACKGROUND

Field

The invention relates to a polyaxial bone anchoring device that includes a bone anchoring element with a head and a shank and a receiving part for coupling the bone anchoring element to a rod. In the receiving part, a pressure element is provided that comprises flexible sections each having an inclined surface portion that cooperates with a corresponding inclined surface portion provided at the receiving part in a configuration in which the flexible sections are flexed to hold the head in an angular position with low friction before the head is locked.

Description of Related Art

US 2010/0234902 A1 describes a receiving part for receiving a rod for coupling the rod to a bone anchoring element. The receiving part includes an accommodation space for accommodating a head of a bone anchoring element and a pressure element arranged at least partially in the accommodation space. In one embodiment, the pressure element has two upstanding resilient fingers and the receiving part comprises two pins to secure the pressure element in the receiving part. The pins form an abutment for the fingers of the pressure element when the pressure element is in a position beneath the pins and the resilient fingers assume their unflexed condition. In this configuration the pressure element exerts a pre-stress or pre-load onto the head that provides a friction fit of the head in the receiving part.

SUMMARY

It is the object of the invention to provide an improved polyaxial bone anchoring device with a friction fit of the head in the receiving part by exerting a pre-load onto the head with a pressure element.

The object is solved by a polyaxial bone anchoring device according to claim 1. Further developments are given in the dependent claims.

The polyaxial bone anchoring device comprises a pressure element that is designed to achieve a friction fit of the head in the receiving part with a low frictional force. This improves the handling of the device during surgery because the receiving part can be pivoted relative to the bone anchoring element by applying a force, for example manually, to the receiving part to align it with the rod to be inserted.

Because the inclined surface portion of the pressure element and the corresponding inclined surface portion of the receiving part are in contact with each other when the pressure element moves downward, a chain of tolerances between the receiving part, the head and the pressure element can be balanced in such a way that a defined pre-load is exerted onto the head. Furthermore, the pre-load exerted via the pressure element onto the head is reproducible, i.e. does not depend on exact dimensions and exact relative positions of the pressure element and the receiving part.

The polyaxial bone anchoring device can be designed as a polyaxial bone anchoring device with an enlarged pivot angle of the anchoring element relative to the receiving part. In this case, the head of the bone anchoring element is seated in a sleeve-like insert piece that is rotatably and pivotably accommodated in the receiving part. With such a configuration, the chain of tolerances includes also the sleeve-like insert piece.

To achieve the friction fit of the head with a low frictional force, additional elements compared to known polyaxial bone anchoring devices are not necessary.

BRIEF DESCRIPTION OF DRAWINGS

Further features and advantages of the invention will become apparent from the description of embodiments using the accompanying drawings. In the drawings.

DETAILED DESCRIPTION

Figure 1:
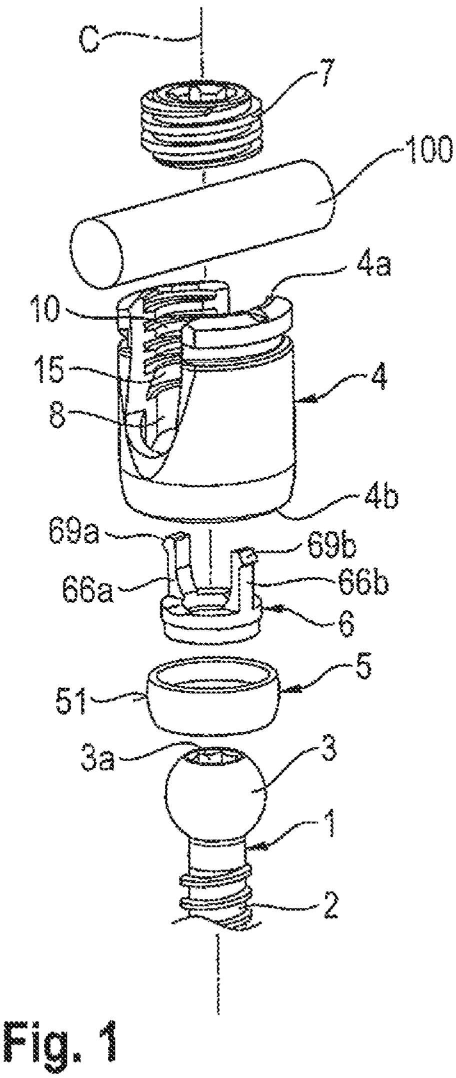
FIG. 1 shows a perspective exploded view of a polyaxial bone anchoring device with a spinal rod according to a first embodiment.
Figure 2:
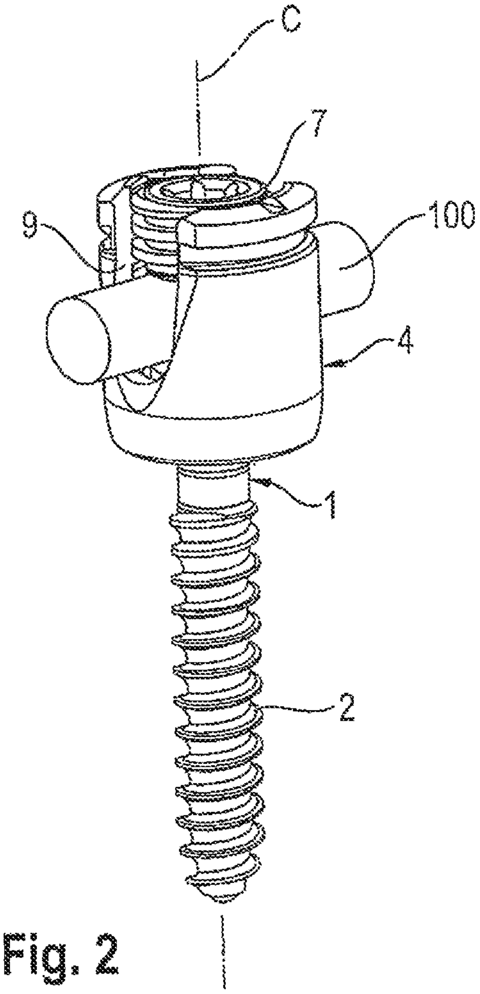
FIG. 2 shows a perspective view of the bone anchoring device of FIG. 1 in an assembled state.

As shown in FIGS. 1 and 2, a polyaxial bone anchoring device according to a first embodiment includes a bone anchoring element 1 in the form of a bone screw having a shank 2 with a threaded portion and a head 3. The head 3 typically has a spherically-shaped outer surface portion and a recess 3*a* at its free end for engagement with a driver or another tool. The head 3 may be held in a receiving part 4 that couples the bone anchoring element 1 to a stabilization rod 100. In the receiving part 4, a sleeve-like insert piece 5 providing a seat for the head 3 and a pressure element 6 for exerting pressure onto the head 3 are arranged. Furthermore, a fixation element in the form of, for example, a fixation screw 7 is provided for securing and fixing the rod 100 in the receiving part 4.

Figure 3:
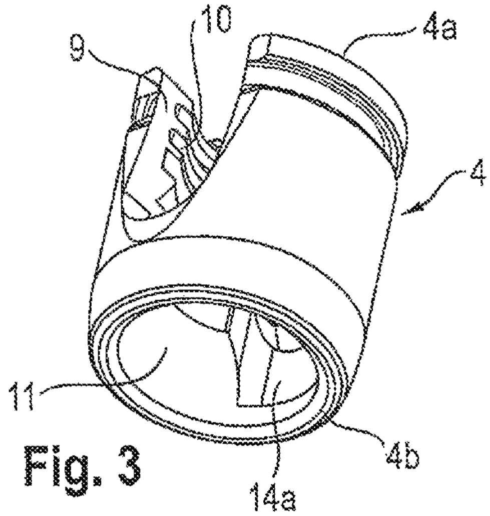
FIG. 3 shows a perspective view from the bottom of the receiving part of the polyaxial bone anchoring device according to the first embodiment.
Figure 4:
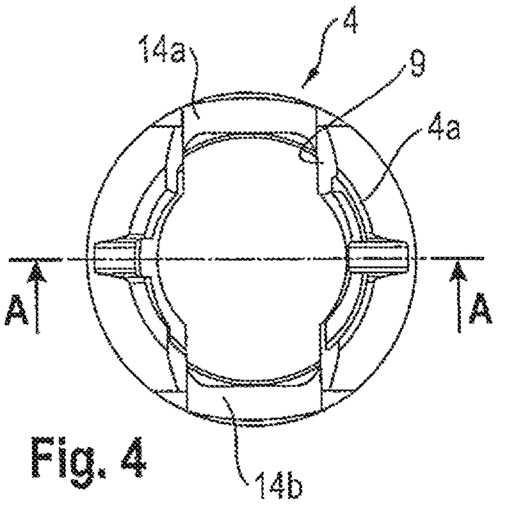
FIG. 4 shows a top view of the receiving part of FIG. 3.
Figure 5:
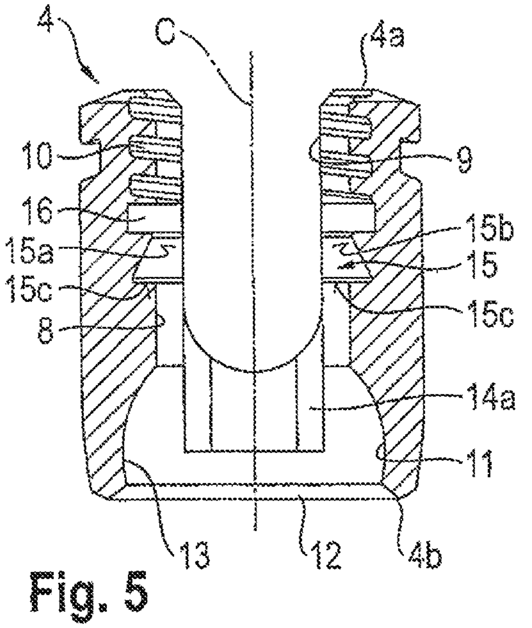
FIG. 5 shows a cross-sectional view of the receiving part along line A-A in FIG. 4.

Referring in particular to FIGS. 3 to 5, the receiving part 4 has a top end 4*a* and a bottom end 4*b*, a central axis C and a coaxial bore 8 extending from the top end 4*a* in the direction of the bottom end 4*b*. Adjacent to the top end 4*a*, a substantially U-shaped recess 9 is provided that forms a channel for receiving the rod 100. By means of the recess 9, two free legs are formed which are provided with an internal thread 10 for cooperating with the fixation screw 7.

The coaxial bore 8 opens into an accommodation space 11 provided in a lower part of the receiving part, e.g. nearer to the bottom end 4*b*. The accommodation space 11 has a lower opening 12 at the bottom end 4*b* of the receiving part. The accommodation space 11 further includes a seat portion 13 near the bottom end 4*b* of the receiving part in which the sleeve-like insert piece 5 may be seated. The seat portion 13 has a spherical shape in order to provide a socket for a ball and socket joint that is formed by the sleeve-like insert piece 5 and the receiving part 4. It should be noted that the seat portion 13 can also be tapered, or can have various other shapes that can be used to realize a ball and socket joint. An inner diameter of the lower opening 12 is smaller than an inner diameter of other portions of the accommodation space 11. It shall also be noted that an inner diameter of the coaxial bore 8 can vary such that the coaxial bore 8 may have different portions with different diameters.

In order to allow the sleeve-like insert piece 5 to be introduced from the top end 4*a*, the receiving part has in the inner wall of the coaxial bore and the accommodation space 11 two recesses 14*a*, 14*b*. The recesses 14*a*, 14*b* are aligned with the U-shaped recess 9 and extend from a bottom of the U-shaped recess 9 into the accommodation space 11. The size of the recesses 14*a*, 14*b* is such that the sleeve-like insert piece can be introduced from the top end 4*a* in a 90° tilted position, i.e. the width of the recesses 14*a*, 14*b* are greater than the height of the sleeve-like insert piece 5 in its axial direction. The recesses 14*a*, 14*b* extend into the accommodation space 11 to such an extent the tilting of the insert piece into the seat 13 is possible.

As can be seen in particular in FIGS. 1 and 5, the receiving part 4 comprises a conically shaped cutout 15 that extends in circumferential direction and is provided in both legs of the receiving part 4. The cutout 15 is located at an axial position with respect to the central axis C that is between the accommodation space 11 and the internal thread 10. The orientation of the conical cutout 15 is such that the cutout 15 widens in a direction towards the bottom end 4*b*, thereby providing on each leg a conically inclined surface portion 15*a*, 15*b* including an angle of inclination $\alpha$ with the central axis C. The angle of inclination $\alpha$ may be, for example, approximately 25° (FIG. 11*b*) or at least less than 70°. A base surface 15*c* of the conical cutout may be oriented perpendicular to the central axis C. A maximum depth of the cutout 15 in a radial direction may be larger the inner diameter of the bore 8. Between the portion with the internal thread 10 and the conical cutout 15 an undercut portion 16 may be provided with an internal diameter that is larger than the inner diameter of the upper edge of the conical cutout 15.

Figure 6:
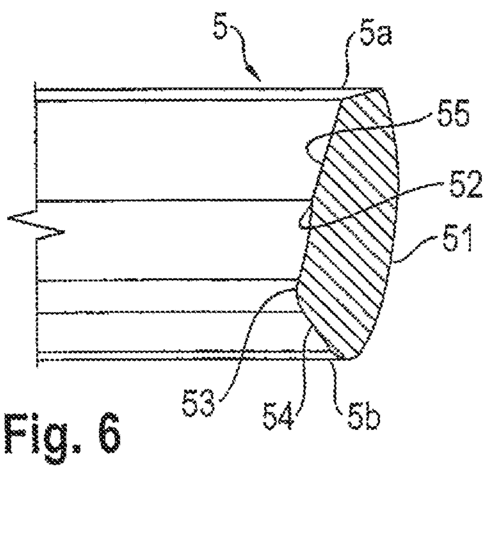
FIG. 6 shows an enlarged cross-sectional view of a portion of a sleeve-like insert piece of the polyaxial bone anchoring device according to the first embodiment.
Figure 11A:
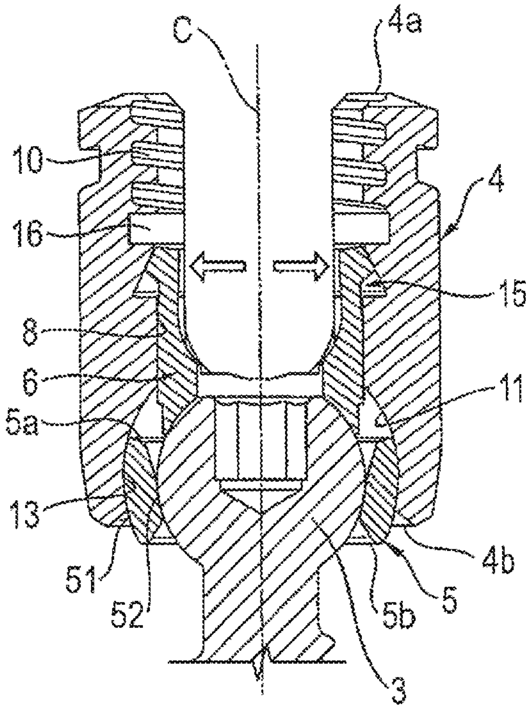
FIG. 11*a* shows a cross-sectional view of the polyaxial bone anchoring device in an assembled state without inserted rod, the section taken along line A-A in FIG. 4 with respect to the receiving part.

The sleeve-like insert piece 5 is shown in particular in FIGS. 1 and 6. The sleeve-insert piece 5 has an upper edge 5*a* and a lower edge 5*b*. Between the upper edge 5*a* and the lower edge 5*b*, a sleeve-like insert piece 5 may have a spherically-shaped outer surface portion 51. A largest outer diameter of the sleeve-like insert piece is greater than the inner diameter of the lower opening 12 of the receiving part 4. Hence, the sleeve-like insert piece 5 cannot escape through the lower opening 12 when it is seated in the receiving part 4. The dimension or shape of the outer spherical surface portion 51 corresponds to that of the spherically-shaped seat portion 13 in the receiving part 4 in such a way that the sleeve-like insert piece 5 can pivot and rotate in the receiving part 4 when the insert piece 5 is seated in the seat portion 13. When the sleeve-like insert piece 5 rests in the seat portion 13 in a coaxial configuration such that its center axis 5*c* is coaxial with the center axis C of the receiving part 4, the lower edge 5*b* projects out of a lower opening 12 as can be seen in FIG. 11*a*. When the sleeve-like insert piece 5 is pivoted or angled in the receiving part, at least a portion of the lower edge 5*b* still projects out of the lower opening 12.

The sleeve-insert piece 5 is hollow and has a central portion 52 that is spherically-shaped with a radius corresponding to a radius of the spherically-shaped outer surface portion of the head 3 of the bone anchoring element 1. A lower end of the central portion 52 forms a shoulder 53, an inner diameter of the shoulder 53 is smaller than a largest outer diameter of the spherical head 3, so that the head 3 can rotate and pivot in the central spherical portion 52 of the sleeve-like insert piece 5, similar to a ball and socket joint. Between the shoulder 53 and the lower edge 5*b*, a tapered portion 54 is provided that tapers outward to allow angulation of the bone anchoring element 1 until the shank 2 comes into contact with the lower edge 5*b*. Between the spherical central portion 52 and the upper edge 5*a*, a tapered portion 55 is provided which also tapers outward. An inner diameter of tapered portion 55 and of a transition between the tapered portion 55 and the spherical central portion 52 are greater than the largest outer diameter of the head 3, so that the head 3 can be inserted from the upper edge 5*a*. A height of the sleeve-like insert piece 5 in an axial direction is less than a height of the head 3 in an axial direction, such that when the head 3 is inserted into the sleeve-like insert piece 5, a portion of the spherical outer surface of the head 3 still projects from the upper edge 5*a* of the sleeve-like insert piece 5.

Figure 7:
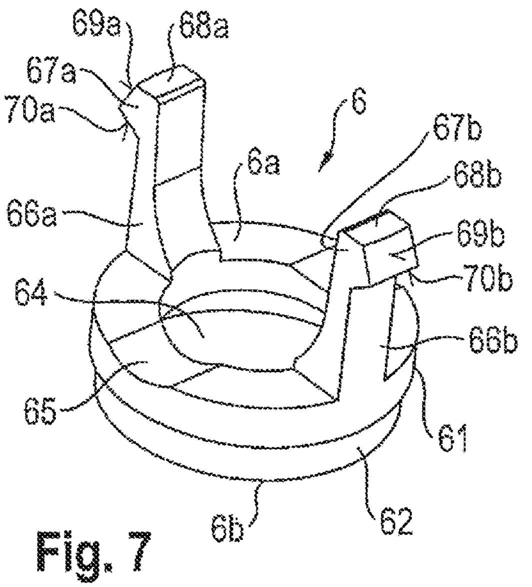
FIG. 7 shows a perspective view from the top of a pressure element of the polyaxial bone anchoring device according to the first embodiment.
Figure 8:
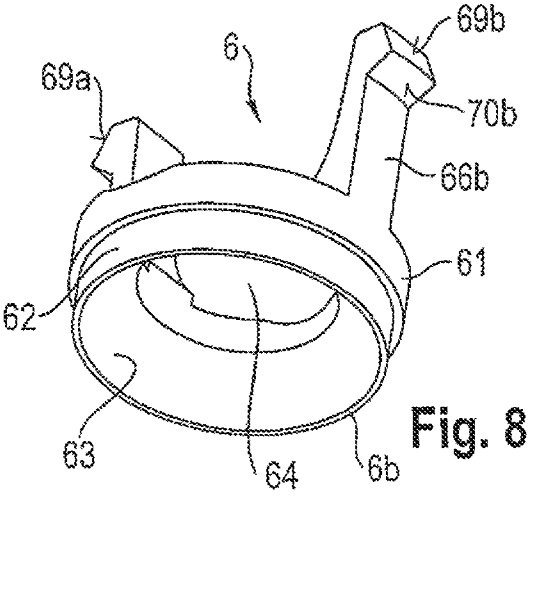
FIG. 8 shows a perspective view from the bottom of the pressure element of FIG. 7.

Referring to FIGS. 7 and 8, the pressure element 6 comprises a main body with a first cylindrical portion 61 with a first outer diameter and a second cylindrical portion 62 with a second outer diameter that is smaller than the first outer diameter. The first cylindrical portion 61 defines an upper surface 6*a* and the second cylindrical portion 62 defines a lower edge 6*b*. A spherical recess 63 is provided adjacent to the lower portion 6*b*. The recess 63 is sized such that it matches the shape of the spherical portion of the head 3. Furthermore, a coaxial through hole 64 extends from the upper surface 6*a* into the recess 63 to allow the access with a tool to engage the recess 4 in the head 3 of the bone anchoring element 1. In the upper surface 6*a*, a shallow substantially cylinder segment-shaped recess 65 may be provided for guiding the rod.

The pressure element further comprises flexible sections in the form of two upstanding resilient fingers 66*a*, 66*b* extending from the upper surface 6*a* upwards. As shown in detail in FIG. 9, the outer wall of the resilient fingers 66*a*, 66*b* is adjacent to the top surface 6*a* substantially flush with the outer surface of the first cylindrical portion 61. The inner surface of the resilient fingers 66*a*, 66*b* is slightly concave in a portion adjacent to the upper surface 6*a* and substantially straight in a portion adjacent to the free end of the fingers. At their free ends, the fingers 66*a*, 66*b* each comprise an outwardly extending portion 67*a*, 67*b*, respectively, including a top surface 68*a*, 68*b* that extends substantially perpendicular to the central axis C and an outer conically inclined surface portion 69*a*, 69*b* wherein the cone widens towards the lower edge 6*b*. The angle of inclination of the inclined surface portion 69*a*, 69*b* with the central axis C is substantially 25°. It can be smaller than the angle of inclination α of the inclined surface portions 15*a*, 15*b* of the receiving part or can be substantially the same. The outwardly extending portion 67*a*, 67*b* further comprises a downwardly facing surface 70*a*, 70*b* with an inclination opposite to the inclination of the inclined surface portion 69*a*, 69*b* that facilitates the insertion of the pressure element into the receiving part 4. The dimensions of the pressure element 6 are such that the first outer diameter of the first cylindrical portion 61 is only slightly smaller than the inner diameter of the coaxial bore 8 so that the pressure element can slide along the inner wall of the coaxial bore 8.

Figure 9:
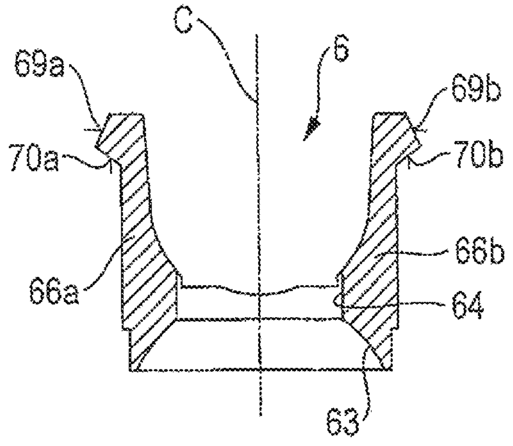
FIG. 9 show a cross-sectional view of the pressure element, wherein the section has been taken in a plane containing the central axis and extending through the middle of resilient fingers of the pressure element in a first, unflexed configuration.
Figure 10:
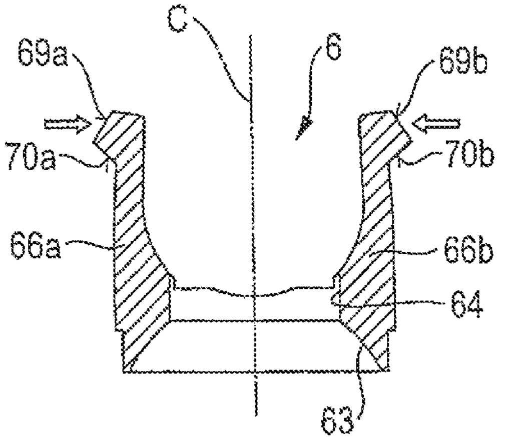
FIG. 10 shows a cross-sectional view of the pressure element in a second, flexed configuration.

As can be seen in the cross-sectional view in FIG. 9, the thickness of the resilient fingers 66*a*, 66*b* in a radial direction is smallest at a position at substantially the middle between the top surface 68*a*, 68*b* of the fingers and the top surface 6*a* of the first cylindrical portion 61. The resilient fingers 66*a*, 66*b* are flexible towards the central axis C in such a manner that they can be slightly bent towards each other as shown in FIG. 10.

When the head 3 with the sleeve-like insert piece 5 is inserted into the receiving part and seated in the seat portion 13 and the pressure element 6 is inserted, the height of the resilient fingers 66*a*, 66*b* is such that the inclined surface portion 69*a*, 69*b* engages an upper portion of the inclined surface portion 15*a*, 15*b* of the conical cutout 15, respectively, as shown in FIG. 11*a*.

The bone anchoring device, as a whole or in parts, is made of a bio-compatible material, such as a bio-compatible metal, for example titanium or stainless steel, a bio-compatible alloy such as Nitinol, or of bio-compatible plastic materials, such as for example, polyetheretherketone (PEEK). The parts may be of the same material or of different material.

The polyaxial bone anchoring device may be pre-assembled. In the following, the steps of assembling the anchoring device are described. First, the sleeve-like insert piece 5 may be introduced from the top end 4*a* into the receiving part 4 in such a manner that the sleeve-like insert piece is tilted by 90° and then introduced into the receiving part so that it extends into recesses 14*a*, 14*b* and thereafter is tilted to assume its position in the seat portion 13. Then the bone anchoring element may be inserted so that the head 3 is seated in the spherical central portion 52 of the sleeve-like insert piece 5.

Figure 11B:
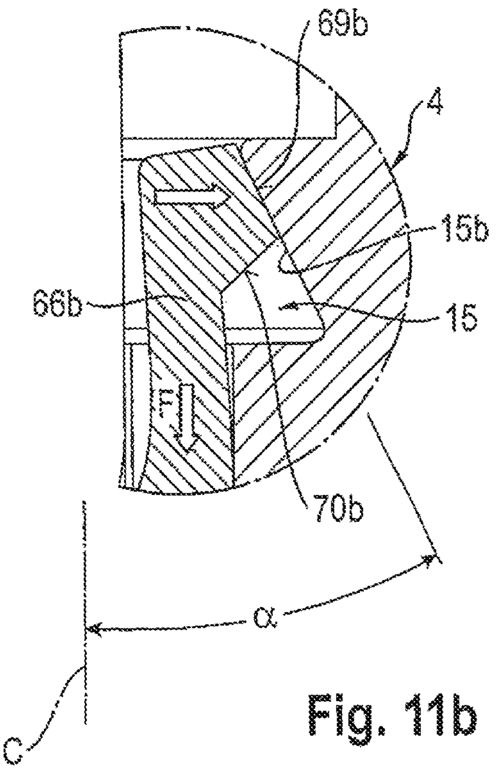
FIG. 11*b* shows an enlarged cross-sectional view of a portion of FIG. 11*a;*

Thereafter, the pressure element is inserted from the top end 4*a* with an orientation such that the resilient fingers are arranged in the U-shaped recess. Then, the pressure element is rotated so that its shallow recess 65 is aligned with the U-shaped recess 9 of the receiving part. The resilient fingers 66*a*, 66*b* are moved into the conical cutout 15. When the inclined portions 69*a*, 69*b* of the resilient fingers engage the inclined surface portion 15*a*, 15*b* of the cutout 15, the fingers are slightly bent inward. Because in this configuration, the resilient fingers 66*a*, 66*b* tend to move apart from each other, a counterforce is generated when the inclined surface portion 69*a*, 69*b* contacts the inclined surface portion 15*a* of the cutout, respectively, as shown in FIG. 11*a*. By the elastic deformation of the resilient fingers 66*a*, 66*b*, a downward axial force F is generated that is transferred via the pressure element 6 onto the head 3 as depicted in FIGS. 11*a* and 11*b*. Hence, a pre-load is applied to the head 3 that holds the head 3 with a low friction force.

Because the surface area of the inclined surface portion 15*a*, 15*b* of the conical cutout 15 is greater than the surface area of the inclined surface portion 69*a*, 69*b*, respectively, the inclined surface portion 69*a*, 69*b* can move along the inclined surface portion 15*a*, 15*b* when the pressure element is moved downward. By means of this, the dimensional tolerances between the head, the sleeve-like insert piece and the pressure element can be balanced by appropriate positioning of the pressure element 6. Therefore, a reproducible, low friction force acting onto the head is generated.

The pressure element may additionally be secured against escaping through the top end 4*a*. For example, the securing can be achieved by crimping (not shown). This may prevent that the pressure element 6 is pushed out through the top end 4*a* because the elastic deformation of the fingers and the generated low friction force may not be sufficient to hold the pressure element in the receiving part in the pre-assembled state.

In use, the pre-assembled polyaxial bone anchoring device is inserted into a bone or a vertebra. Typically, at least two bone anchoring devices are used and connected with the rod 100. The receiving parts are aligned by rotating and/or pivoting them with respect to the bone anchoring elements. The pre-load exerted onto the head can be overcome by manually rotating and/or pivoting the receiving part. Because of the low friction between the head and the pressure element, the anchoring device is convenient to handle.

Because the sleeve-like insert piece 5 is rotatable and pivotable within the receiving part 4, the polyaxial bone anchoring device has an enlarged range of angulation that can be achieved at any position within 360° of the receiving part 4 with respect to the bone anchoring element 1. When the receiving part 4 is pivoted with respect to the bone anchoring element 1, the shank 2 of the bone anchoring element 1 comes into contact with the lower edge 5*b* of the sleeve-like insert piece, the sleeve-like insert piece 5 is also pivoted with the bone anchoring element 1. The shank 2 may push the insert piece 5 until the shank 2 abuts against the edge of the lower opening 12 of the receiving part 4. The maximum pivot angle that can be achieved depends on the dimensions of the sleeve-like insert piece 5, the receiving part 4 and the bone anchoring element 1, but is typically equal to or greater than 45° measured from a straight or zero angle position between the receiving part 4 and the bone anchoring element 1.

After alignment of the receiving parts, the rod 100 is inserted into the channel and then the fixation screw 7 is inserted and tightened. Thereby, the pressure element is moved downward slightly and presses the head 3 into the seat and the sleeve-like insert piece into the seat portion 13. The inner screw 7 is inserted and tightened and the pressure element and the rod are locked.

A polyaxial bone anchoring device according to a second embodiment will be described with reference to FIGS. 12 to 18*b*. Parts and portions which are the same or similar to those of the first embodiment are designated with the same reference numerals, and the descriptions thereof are not repeated. The bone anchoring device of the second embodiment differs from the bone anchoring device of the first embodiment by the construction of the receiving part and the pressure element. All other parts may be identical or similar to those of the first embodiment.

Figure 12:
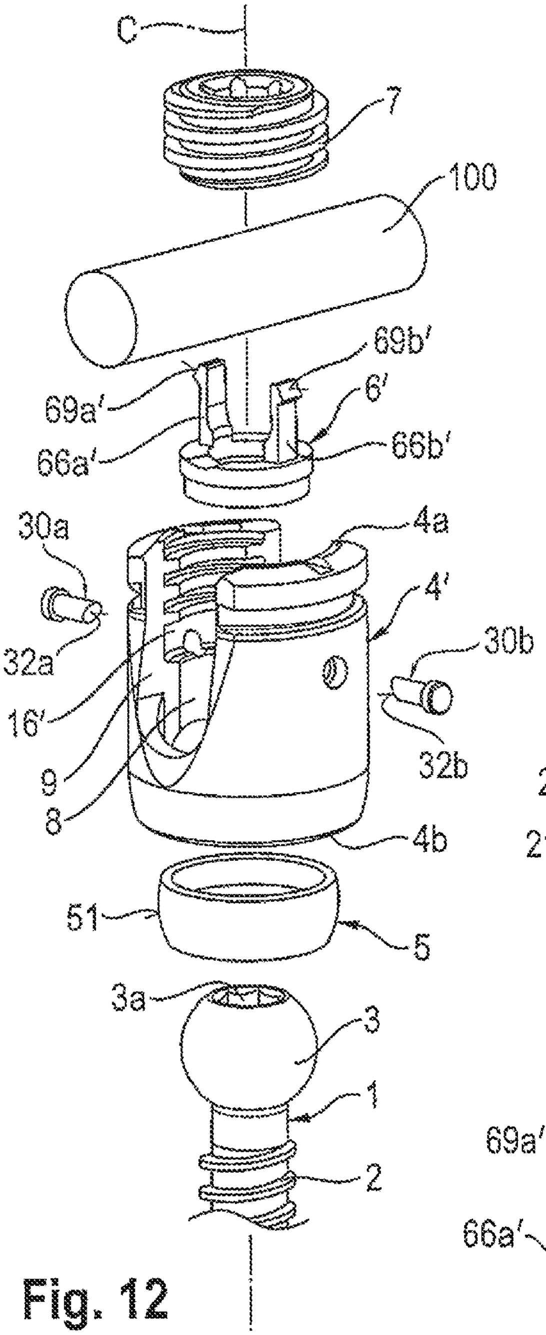
FIG. 12 shows a perspective exploded view of the polyaxial bone anchoring device with a spinal rod according to a second embodiment.
Figure 13:
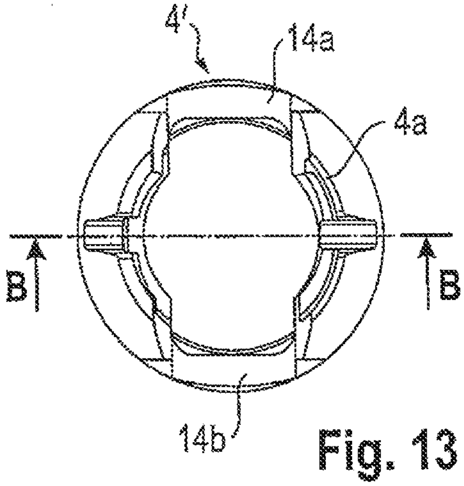
FIG. 13 shows a top view of the receiving part according to the second embodiment.
Figure 14:
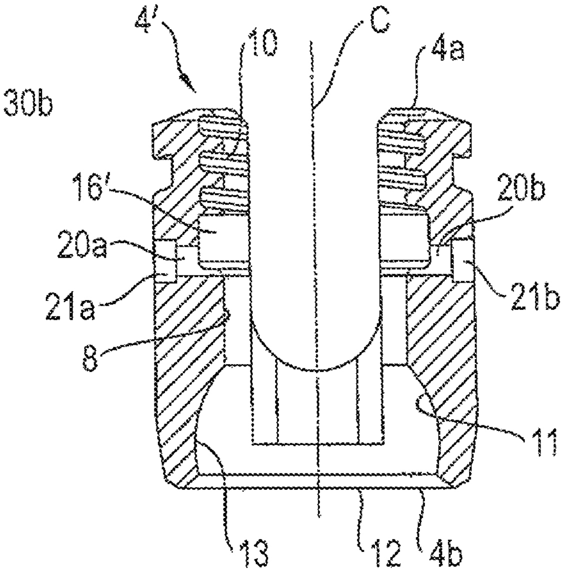
FIG. 14 shows a cross-sectional view of the receiving part along line B-B in FIG. 13.
Figure 15:
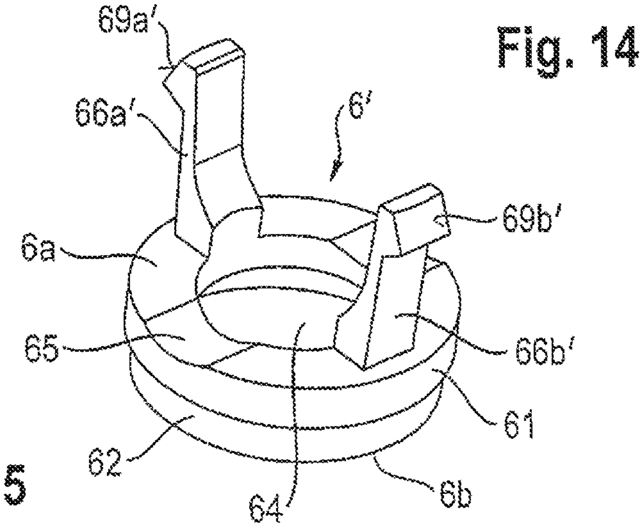
FIG. 15 shows a perspective view of the pressure element of the polyaxial bone anchoring device according to the second embodiment.
Figure 16:
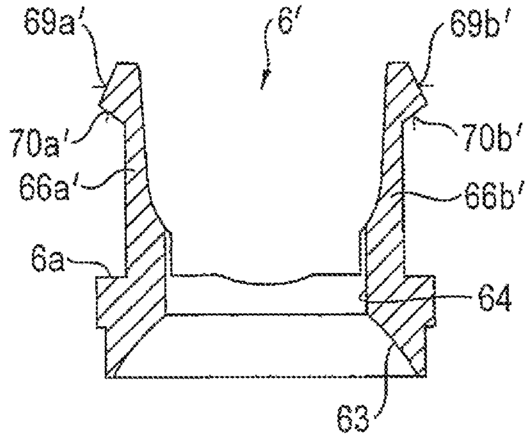
FIG. 16 shows a cross-sectional view of the pressure element in a first, unflexed configuration, wherein the section has been taken in a plane containing the central axis and extending through the middle of the resilient fingers of the pressure element.
Figure 18A:
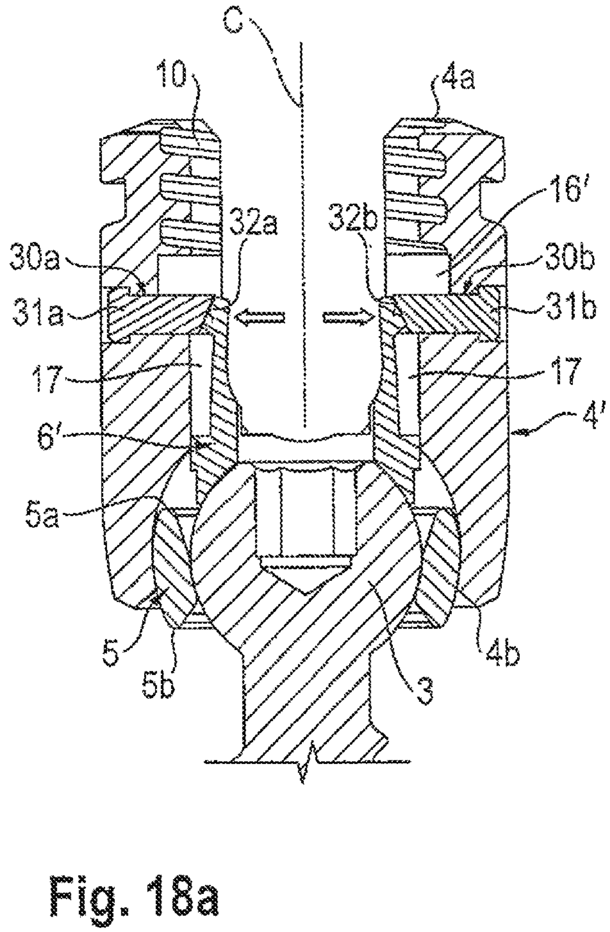
FIG. 18*a* shows a cross-sectional view of the polyaxial bone anchoring device according to the second embodiment without an inserted rod, wherein the section has been taken along line B-B in FIG. 13 with respect to the receiving part.
Figure 18B:
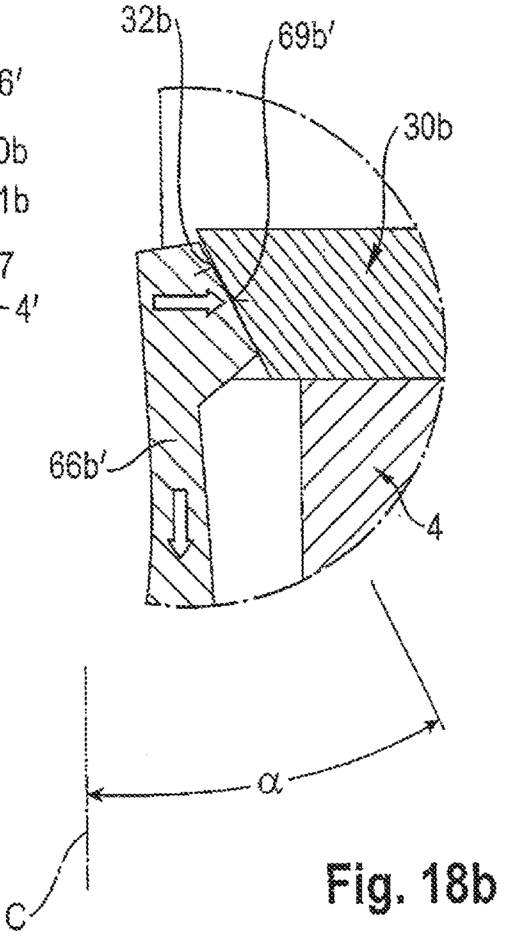
FIG. 18*b* shows an enlarged cross-sectional view of a portion of FIG. 18*a;*

As shown in FIGS. 12 to 14, the receiving part 4' has an undercut portion 16' but no conical cutout. At the lower end of the undercut portion 16' two opposed transverse bores 20*a*, 20*b* extend fully through the wall of the receiving part and open into the undercut portion 16'. The bores 20*a*, 20*b* may have an enlarged section 21*a*, 21*b* with a greater diameter adjacent to the outside. Two pins 30*a*, 30*b* with a head portion 31*a*, 31*b* may be arranged in the bores 20*a*, 20*b* such that the head portions 31*a*, 31*b* rest in the enlarged portions 21*a*, 21*b* as depicted in FIG. 18*a*. When the pins are inserted, they may form a part of the receiving part. The free end of the pins that extends into the inside of the receiving part has an inclined surface portion 32*a*, 32*b*, respectively. The inclined surface portions 32*a*, 32*b* may be flat, i.e. not conical when compared to the first embodiment. The arrangement of the pins 30*a*, 30*b* is such that the distance between the pins along the inclined surface portions 32*a*, 32*b* increases towards the bottom end 4*b* when the pins are inserted into the bores. The angle of inclination is approximately 50° or less measured with respect to the central axis C. The pins extend to such a length into the inside of the receiving part that the corresponding inclined surface portions 69*a*, 69*b* of the pressure element can press against the inclined surface portions 32*a*, 32*b*.

The pressure element 6' has resilient fingers 66*a*', 66*b*' the outer surface of which is not flush with the outer surface of the first cylindrical portion 61 but is offset from the outer surface of the first cylindrical portion. Hence, when the pressure element 6' is inserted into the receiving part, there is a space 17 between the inner wall of the coaxial bore 8 and the outside of the resilient fingers 66*a*', 66*b*'. The inclined surface portions 69*a*', 69*b*' of the fingers are flat in this embodiment.

Figure 17:
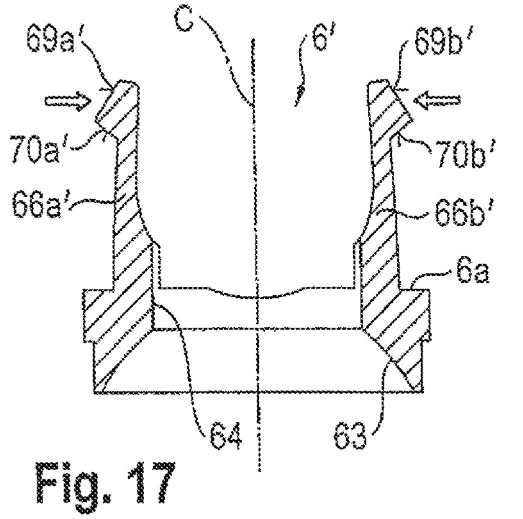
FIG. 17 shows a cross-sectional view of the pressure element in a second, flexed configuration.

The resilient fingers 66*a*', 66*b*' are flexible towards the central axis C as shown in FIG. 17. When the pressure element 6' is inserted into the receiving part 4' that has the pins 30*a*, 30*b* mounted into the bores 20*a*, 20*b*, the inclined surface portions 69*a*, 69*b* come into engagement with the inclined surface portions 32*a*, 32*b* of the pins and the resilient fingers are slightly bent inward. In this configuration, the pressure element 6' exerts a preload onto the head 3 that holds the head 3 in the sleeve-like insert piece and in the seat portion 13 with a low friction force. When the pressure element 6' is further pressed down onto the head during tightening of the fixation screw, the inclined surface portions 69*a*, 69*b* slide along the inclined surface portions 32*a*, 32*b* of the pins, respectively. The outermost edge of the resilient fingers can extend into the space 17 when it is no longer in contact with the inclined surface portion 32*a*, 32*b*.

A polyaxial bone anchoring device according to a third embodiment will be described with reference to FIGS. 19 to 28*b*. Parts and portions which are the same or similar to those of the first and second embodiment are designated with the same reference numerals and the descriptions thereof are not repeated. The bone anchoring device of the third embodiment differs from the bone anchoring device of the first and second embodiments by the design of the receiving part and the pressure element. All other parts may be identical or similar to those of the first and second embodiments.

Figure 19:
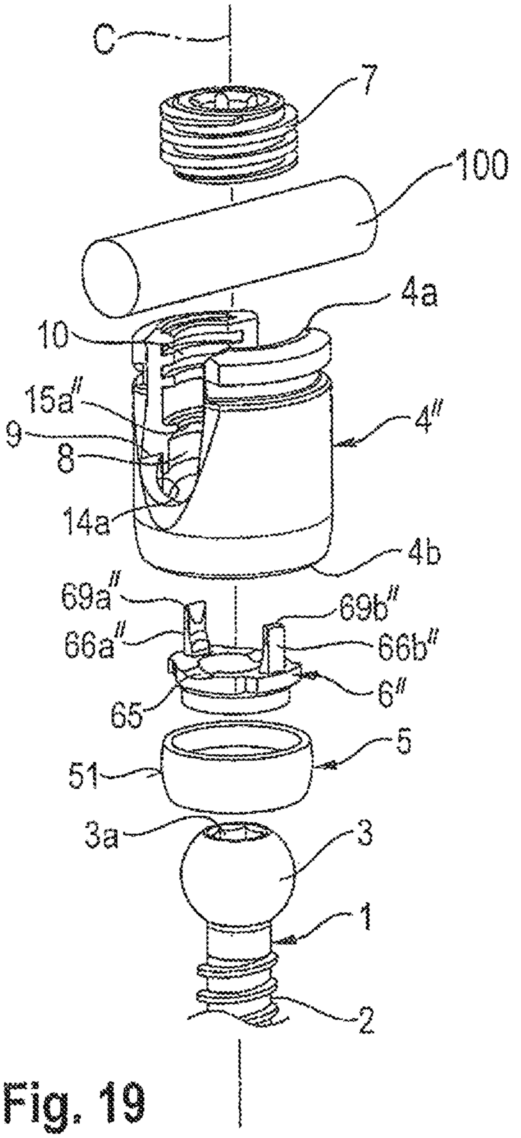
FIG. 19 shows a perspective exploded view of a polyaxial bone anchoring device with a spinal rod according to a third embodiment.
Figure 20:
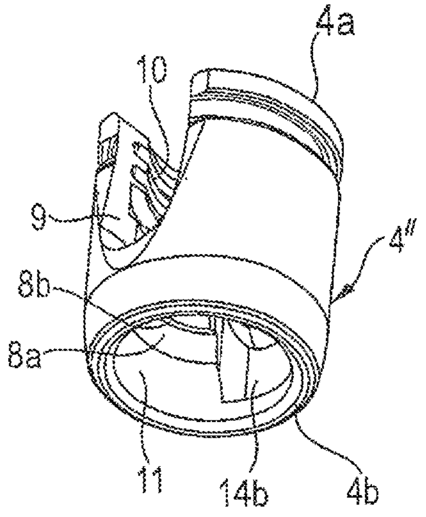
FIG. 20 shows a perspective view from the bottom of the receiving part of the polyaxial bone anchoring device according to the third embodiment.
Figure 21:
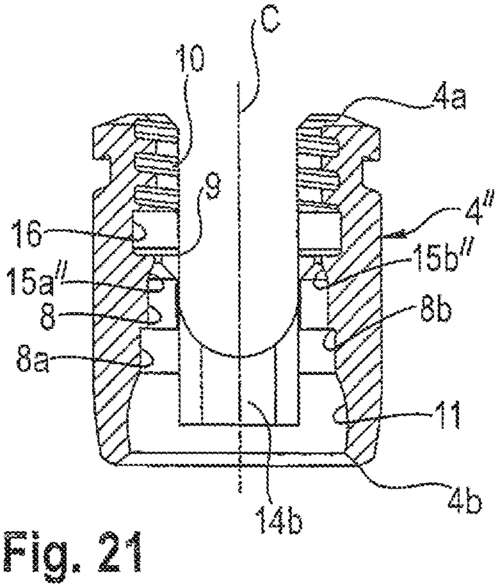
FIG. 21 shows a cross-sectional view of the receiving part of FIG. 20, the cross section taken in a plane through the central axis and perpendicular to the rod axis.
Figure 22:
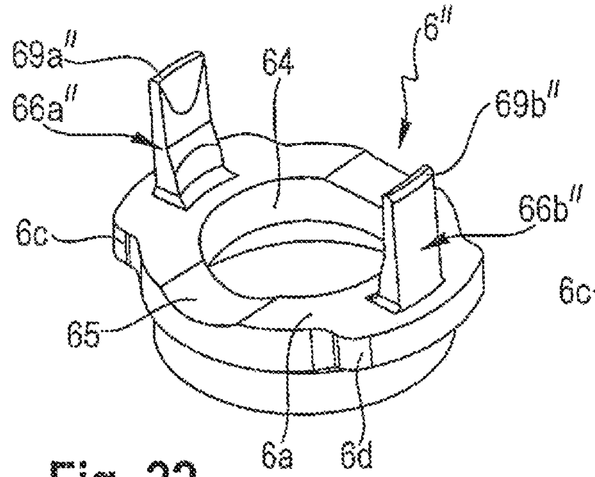
FIG. 22 shows a perspective view of the pressure element of FIG. 19.
Figure 23:
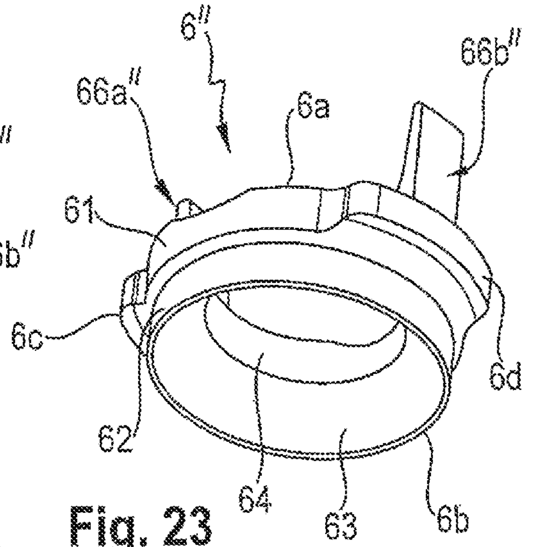
FIG. 23 shows another perspective view from the bottom of the pressure element of FIG. 19.
Figure 24:
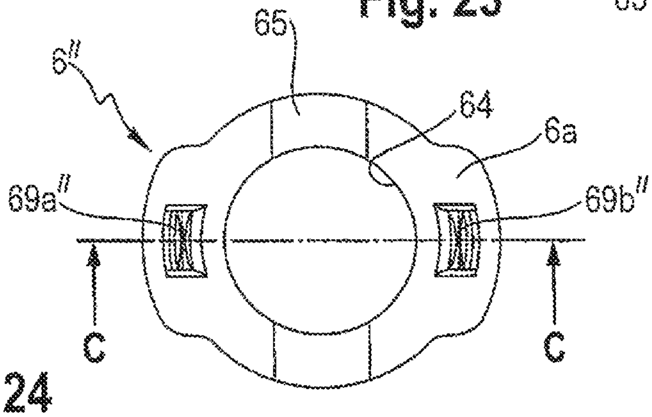
FIG. 24 shows a top view of the pressure element of FIG. 19.

As shown in FIGS. 19 to 21, the receiving part 4" comprises inclined surface portions 15*a*", 15*b*" at the inner side wall of the free legs formed by the U-shaped recess 9.

The inclined surface portions 15$a$", 15$b$" are provided by a conical shape of the bore narrowing towards the top end 4$a$. Hence, the inclined surface portion 15$a$" and 15$b$" are arranged between the undercut 16 and the coaxial bore 8. They serve for cooperation with the resilient fingers of the pressure element 6" as described below. Between the coaxial bore 8 and the accommodation space 11 there is a second coaxial cylindrical bore portion 8$a$ with a larger diameter than the diameter of the coaxial bore 8. By means of this a stop 8$b$ is provided that extends in a circumferential direction and serves as an abutment for a portion of the pressure element 6" to limit an upward movement of the pressure element. The stop 8$b$ is formed monolithically with the receiving part 4". A separate crimping step to secure the pressure element 6" is therefore not needed.

Referring to FIGS. 22 to 26, the pressure element 6" comprises a main body with a cylindrical portion 62 adjacent to the lower edge 6$b$. Following the cylindrical portion 62, there is an upper portion 61 defining the upper surface 6$a$ and comprising the cylinder segment-shaped recess 65 for guiding the rod 100. From the upper portion 61 two lateral projections 6$c$, 6$d$ are provided that extend at 90° with respect to a longitudinal axis of the recess 65. From the lateral projections 6$c$, 6$d$ two resilient fingers 66$a$", 66$b$" extend upwards from the upper surface 6$a$. A spherical recess 63 is provided adjacent to the lower edge 6$b$ as in the first and second embodiments. Furthermore, a coaxial through-hole 64 extends from the upper surface 6$a$ into recess 63 to allow the access with a tool to engage the head 3 of the bone anchoring element 1.

The resilient fingers 66$a$", 66$b$" have a decreasing thickness in radial direction towards their free ends, respectively, to provide sufficient resiliency. They are arranged at approximately the center of the lateral projection 6$c$, 6$d$ so that a portion of the upper surface 6$a$ surrounds the outside of the resilient fingers 6$a$", 6$b$". The upper free end 69$a$", 69$b$" of the resilient fingers 66$a$", 66$b$" is rounded in such a manner that an angle between an upper free end 66$c$ of the resilient finger 66$a$" and the outer surface 66$e$ of the resilient finger 66$a$" is approximately 90° and the edge 69$a$" between the upper free end 66$c$ and the outer surface 66$e$ is rounded. In the same way an angle between the upper free end 66$d$ of the second resilient finger 66$b$" and the outer surface 66$f$ of the second resilient finger 66 $b$" is approximately 90° and the edge 69 $b$" there between is rounded. As a result, the rounded edges 69$a$", 69$b$" act as inclined surface portions that cooperate with the inclined surface portions 15$a$" 15$b$" of the receiving part 4". The inclined surface portion of the rounded edges 69$a$", 69$b$" may be composed of infinitesimally small surface portions that have an inclination with respect to the outer surface 66$e$, 66$f$ of the resilient fingers.

An outer diameter of the pressure element 6" in the region of the lateral projection 6$c$, 6$d$ is greater than an inner diameter of the coaxial bore 8, but smaller than an inner diameter of the second cylindrical bore portion 8$a$ so that the pressure element 6" fits into the receiving part 4" in such a manner that the lateral projections 6$c$, 6$d$ can be housed in the second cylindrical bore portion 8$a$ in the assembled state and the resilient fingers extend into the coaxial bore 8.

Figure 25:
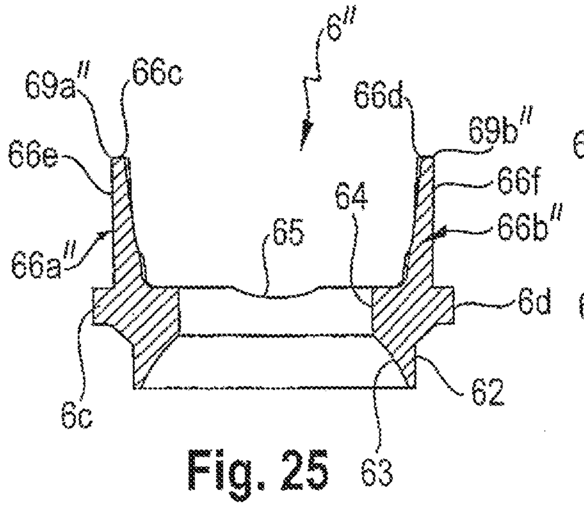
FIG. 25 shows a cross-sectional view of the pressure element of FIGS. 19 and 22 along line C-C in FIG. 24 wherein the pressure element is in the first, unflexed configuration.
Figure 26:
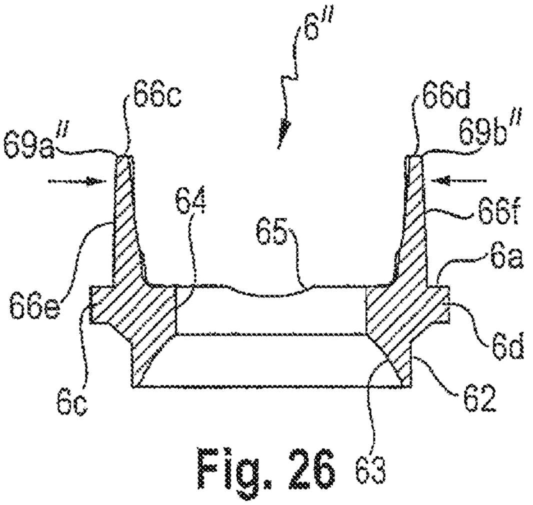
FIG. 26 shows a cross-sectional view of the pressure element along line C-C in FIG. 24, wherein the pressure element is in a second, flexed configuration.
Figure 27A:
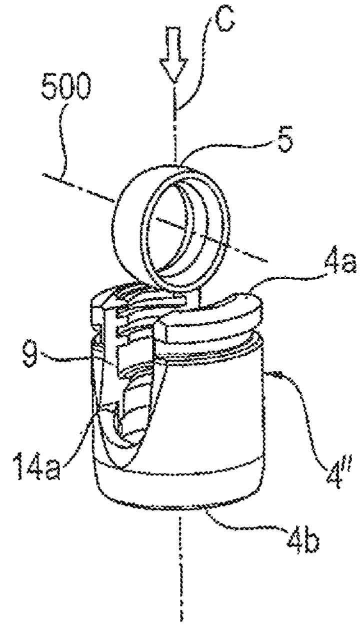
FIGS. 27*a* to 27*f* show steps of assembling the polyaxial bone anchoring device according to the third embodiment.
Figure 27B:
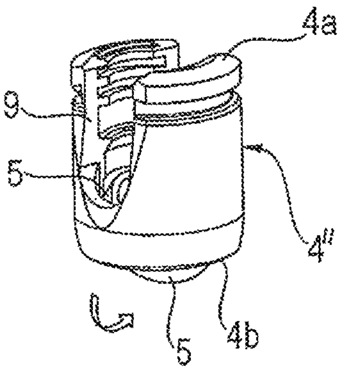
Figure 27C:
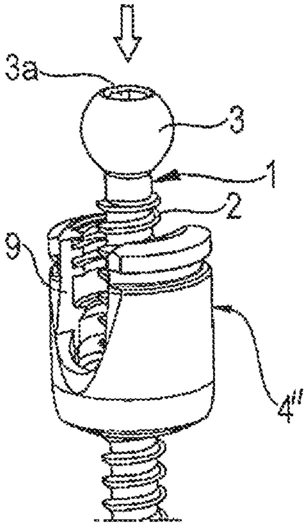
Figure 27D:
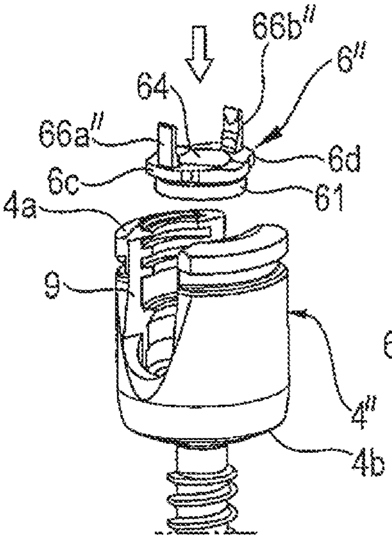
Figure 27E:
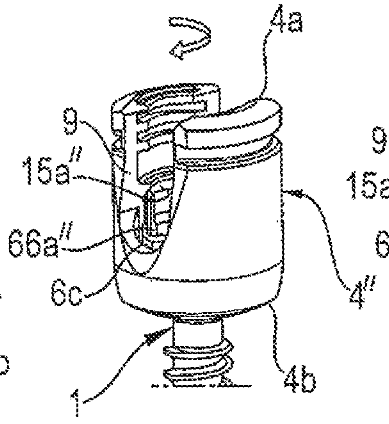
Figure 27F:
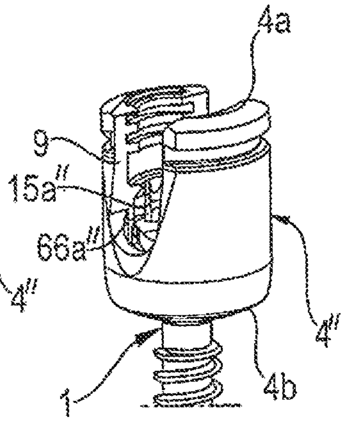

As shown in FIGS. 25 and 26, the resilient fingers 66$a$", 66$b$" are resilient in such a manner that they can be bent slightly inwards from a first configuration shown in FIG. 25 where the fingers are unflexed to a second configuration shown in FIG. 26 where the fingers are flexed inwards, when a radical force shown by the arrows acts on the fingers.

The steps of assembling the polyaxial bone anchoring device according to the third embodiment will be described referring to FIGS. 27$a$ to 27$f$. In a first step shown in FIG. 27$a$ the sleeve-like insert piece 5 is tilted by 90° so that its central axis 500 is perpendicular to the central axis C of the receiving part. In this orientation it is inserted into the receiving part 4" from the top end 4$a$ such that its central axis 500 is also perpendicular to the channel axis of the U-shaped recess 9. Because the sleeve-like insert piece can be inserted into the recesses 14$a$, 14$b$ of the receiving part 4" shown in FIGS. 19 and 21, it can be moved downward until it has reached to accommodation space 11. Then, as shown in FIG. 27$b$, the sleeve-like insert piece 5 is tilted so that its central axis is coaxial with the central axis C of the receiving part and the sleeve-like insert piece 5 is accommodated in the accommodation space 11.

Thereafter, as shown in FIG. 27$c$, the bone anchoring element 1 is introduced from the top end 4$a$ into the receiving part 4" so that the threaded shank 2 extends through the lower opening and finally the head 3 is received in the sleeve-like insert piece 5.

Figure 28A:
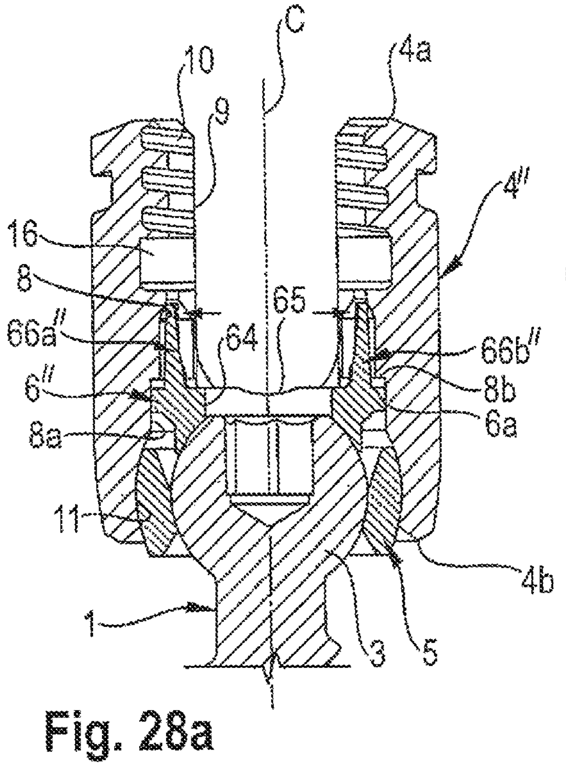
FIG. 28*a* shows a cross-sectional view of the polyaxial bone anchoring device according to the third embodiment without an inserted rod, the section taken in a plane containing the central axis and extending through the middle of the resilient fingers of the pressure element.
Figure 28B:
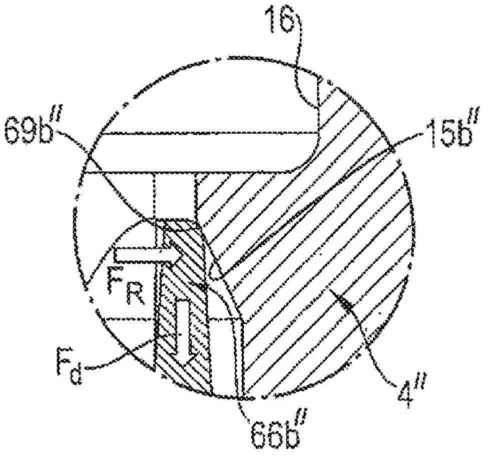
FIG. 28*b* shows an enlarged cross-sectional view of a portion of FIG. 28*a;*

Then, the pressure element 6" is inserted into the receiving part from the top end 4$a$ such that the resilient fingers 66$a$", 66$b$" extend upwards in the direction of the top end 4$a$ and the lateral projections 6$c$, 6$d$ extend into the direction of the channel axis of the U-shaped recess 9. Therefore, the pressure element 6" can be inserted with its lateral projection 6$c$, 6$d$ engaging the recesses 14$a$, 14$b$ of the receiving part 4" until the pressure element 6" reaches with its upper portion 61 the second coaxial bore portion 8$a$ as shown in FIG. 28$a$. As shown in FIG. 27$e$, the pressure element 6" is then rotated so that the lateral projection 6$c$, 6$d$ are moved below the stops 8$b$ and are accommodated in the second cylindrical bore portion 8$a$ as depicted in FIG. 28$a$. Due to the stops 8$b$ an upward movement of the pressure element 6" is limited until a portion of the upper surface 6$a$ abuts the stop 8$b$ in the receiving part 4".

In the assembled state as shown in FIGS. 27$f$, 28$a$ and 28$b$, the resilient fingers 66$a$", 66$b$" extend through the coaxial bore 8 such that their upper rounded edges 69$a$", 69$b$" abut against the uppermost portion of the inclined surface portions 15$a$", 15$b$" of the receiving part 4", thereby being slightly flexed inwards.

In this configuration shown in detail in FIGS. 28$a$ and 28$b$, the resilient fingers 66$a$", 66$b$" press onto the inclined surface portion 15$a$", 15$b$" with a force $F_r$ shown by the arrow. They experience a counterforce from the inclined surface portions 15$a$", 15$b$" of the receiving part 4" and as a result an axial downward force $F_a$ shown by the arrow acts onto the head 3 which clamps the head 3 by a low frictional force. Hence, a pre-load is applied to the head 3 that holds the head 3 in a certain angular position.

As in the previous embodiments, when the pressure element is moved downward, the rounded edge 69$a$", 69$b$" move along the inclined surface portion 15$a$", 15$b$". By means of this, the dimensional tolerances between the head 3, the sleeve-like insert piece 5 and the pressure element 6" can be balanced by appropriate positioning of the pressure element 6". Also in this embodiment, a reproducible low friction force acting onto the head 3 is generated. The rounded edges 69$a$", 69$b$" slide smoothly along the inclined surface portions 15$a$", 15$b$" of the receiving part without being jammed.

Figure 29A:
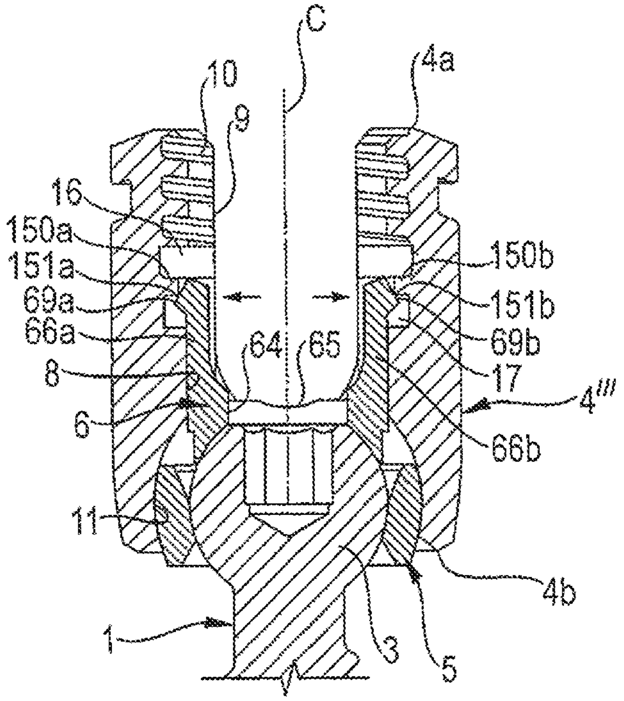
FIG. 29*a* shows a cross-sectional view of a polyaxial bone anchoring device according to a fourth embodiment without an inserted rod, the section taken in a plane containing the central axis and extending through the middle of the resilient fingers of the pressure element.
Figure 29B:
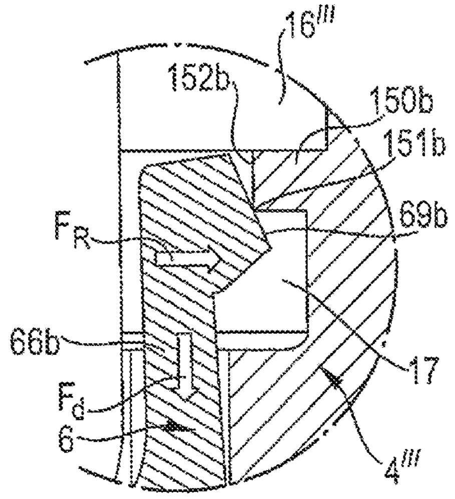
FIG. 29*b* shows an enlarged cross-sectional view of a portion of FIG. 29*a.*

A polyaxial bone anchoring device according to a fourth embodiment will be described with reference to FIGS. 29$a$ and 29$b$. Parts and portions which are the same or similar to those of the first and second embodiment are designated with the same reference numerals and the descriptions thereof are not repeated. The bone anchoring device of the fourth embodiment comprises the pressure element 6 as in the first embodiment that comprises the outwardly inclined surfaces 69*a*, 69*b* at the upper end of the resilient fingers 66*a*, 66*b*. It shall be noted that the pressure element 6' of the second embodiment can also be used in the fourth embodiment of the polyaxial bone anchoring device. The receiving part 4''' of the fourth embodiment differs from the receiving part of the first to third embodiments. All other parts may be identical or similar to those of the first to third embodiments.

The receiving part 4''' comprises a first undercut portion 16''' adjacent to the thread 10 and a second undercut portion 17 at a distance from the first undercut portion 16''' in the direction towards the bottom end 4*b*. Between the undercut portions there is a circumferentially extending projection 150*a*, 150*b* on each of the legs that projects towards the central axis C. The projection 150*a*, 150*b* has a substantially rectangular cross section so that a lower rectangular edge 151*a*, 151*b* is formed that may be rounded. An inner surface 152*a*, 152*b* of the projection is substantially coaxial with the central axis C. The size of the projections 150*a*, 150*b* is such that when the pressure element is inserted and placed onto the head 3, the inclined surfaces 69*a*, 69*b* abut against the edge 151*a*, 151*b* and the resilient fingers are slightly bent inwards. Through the resulting counterforce a downward axial force $F_d$ is generated that acts onto the head such that the head is held by friction in a specific angular position.

Therefore, for all embodiments, through the interaction of on inclined surface or an edge provided on the pressure element or on the receiving part on the one side and an edge or another inclined surface at the corresponding position of the receiving part or the pressure element on the other side, a downward force is generated that holds the head by a low friction force. The inclined surface portions 15*a*, 15*b*; 32*a*, 32*b*; 15*a''*, 15*b''*, 69*a*, 69*b*, 69*a'*, 69*b'* of either the pressure element or the receiving part have an upper end that is closer to the top end 4*a* of the receiving part and a lower end that is closer to the bottom end 4*b* of the receiving part when the pressure element is arranged in the receiving part and the inclination is such that the upper end is closer to the central axis C than the lower end.

Modifications of the embodiments described may also be made. For example, more than two resilient fingers may be present. In the second embodiment, more than two pins may be present according to the number of resilient fingers. In a further modification, only one single flexible section may be provided on the pressure element. The lower portion of the pressure element may be designed differently. The sleeve-like insert piece may be omitted. In this case, the accommodation space of the receiving part may be smaller and the head may be seated directly in the seat portion of the receiving part. The receiving part may be constructed so as to allow the insertion of the bone anchoring element from the bottom end. Also, the pressure element may be constructed so as to allow the insertion into the receiving part from the bottom end. Furthermore, the inclined surface portions need not to be conically-shaped as in the first embodiment or flat as in the second embodiment. they may have any shape which allows to generate a downward force.

For the bone anchoring element, various different kinds of anchoring elements can be used and combined with the receiving part. These anchoring elements may be, for example, screws with different length, screws with different diameters, cannulated screws, screws with different thread forms, nails, hooks etc. For some anchoring elements, the head and the shaft may also be separate parts that are connectable to each other.

Other kinds of locking devices including outer nuts, outer caps, bayonet locking devices, or others are also possible. Also, a two part locking device may be used with an outer locking device that acts onto the pressure element only and an inner locking device that presses onto the rod. The inner surface portion of the pressure element may have any other shape that is suitable to exert pressure onto the head.

It shall also be noted that portions of the different described embodiments can also be combined with each other in various different combinations.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:

a bone anchoring element comprising a shank and a head comprising a spherical segment-shaped portion;

a receiving part for coupling a rod to the bone anchoring element, the receiving part having a first end, a second end below the first end, a central axis extending between the first and second ends, a channel at the first end for receiving the rod, and an accommodation space at the second end for pivotably receiving the head with at least part of the spherical segment-shaped portion of the head directed downwardly to facilitate the pivotability of the head relative to the receiving part;

a ring-shaped member positionable in the receiving part; and a separate flexible member positionable in the receiving part, the flexible member comprising an engagement surface configured to engage the receiving part and a flexible portion that extends axially downwardly from the engagement surface;

wherein when the head, the ring-shaped member, and the flexible member are in the receiving part, the head is pivotable relative to the ring-shaped member, part of the ring-shaped member is configured to form an uninterrupted closed ring around the central axis that is positioned lower axially than an axial position of a greatest diameter of the spherical segment-shaped portion of the head measured in a direction perpendicular to the central axis, and the head is movable axially upwardly relative to the receiving part while the flexible member is configured to exert a downward axial force to urge the head back down axially.

2. The bone anchoring device of claim 1, wherein the ring-shaped member is configured to engage the head in the receiving part.

3. The bone anchoring device of claim 2, wherein the ring-shaped member forms a seat configured to hold the head in the receiving part.

4. The bone anchoring device of claim 1, wherein the ring-shaped member is pivotable relative to the receiving part.

5. The bone anchoring device of claim 1, wherein the receiving part defines an opening at the second end, and wherein a smallest diameter of the opening is greater than the greatest diameter of the head.

6. The bone anchoring device of claim 1, wherein an inner diameter of the uninterrupted closed ring of the ring-shaped member that is positioned lower axially than the greatest diameter of the head is smaller than the greatest diameter of the head.

7. The bone anchoring device of claim 1, wherein the flexible member is configured to urge a head contacting surface of a pressure element against the head to clamp the head in the receiving part.

8. The bone anchoring device of claim 7, wherein the flexible member is monolithically formed with the pressure element.

9. The bone anchoring device of claim 1, wherein the flexible member is positionable higher axially in the receiving part than the entire ring-shaped member.

10. The bone anchoring device of claim 1, wherein when the head, the ring-shaped member, and the flexible member are in the receiving part, the head is tiltable relative to the ring-shaped member.

11. A bone anchoring device comprising:

a bone anchoring element comprising a shank and a head comprising a spherical segment-shaped portion;

a receiving part for coupling a rod to the bone anchoring element, the receiving part having a first end, a second end below the first end, a central axis extending between the first and second ends, a channel at the first end for receiving the rod, and an accommodation space at the second end for pivotably receiving the head with at least part of the spherical segment-shaped portion of the head directed downwardly to facilitate the pivotability of the head relative to the receiving part;

a ring-shaped member positionable relative to the receiving part such that part of the ring-shaped member forms an uninterrupted closed ring around the central axis that is positioned lower axially than a bottommost end of the receiving part; and a separate clamping member configured to engage and exert a clamping force on the head in the receiving part, the clamping member comprising a flexible portion;

wherein the head is insertable into the receiving part while a shape of the entire receiving part remains constant, to a position where at least part of the receiving part extends lower axially than an axial position of a greatest diameter of the spherical segment-shaped portion of the head measured in a direction perpendicular to the central axis;

wherein when the head, the ring-shaped member, and the clamping member are assembled to the receiving part, the head is pivotable relative to the ring-shaped member, while a radially innermost part of the flexible portion is urged radially inwardly to hold the clamping member against the head to exert the clamping force on the head.

12. The bone anchoring device of claim 11, wherein the ring-shaped member is insertable into the receiving part.

13. The bone anchoring device of claim 11, wherein the ring-shaped member restricts removal of the head from the second end of the receiving part.

14. The bone anchoring device of claim 11, wherein the ring-shaped member and the clamping member are configured to be completely spaced apart from one another in the receiving part.

15. The bone anchoring device of claim 11, wherein the clamping member is formed as a pressure element configured to exert a downwardly directed force on the head.

16. The bone anchoring device of claim 11, wherein the flexible portion of the clamping member is configured to be spaced apart from the head in the receiving part.

17. The bone anchoring device of claim 11, wherein the clamping member is positionable higher axially in the receiving part than the entire ring-shaped member.

18. The bone anchoring device of claim 11, wherein when the head, the ring-shaped member, and the clamping member are assembled to the receiving part, the head is tiltable relative to the ring-shaped member.

19. A bone anchoring device comprising:

a bone anchoring element comprising a head and a shank;

a receiving part for coupling a rod to the bone anchoring element, the receiving part having a first end, a second end below the first end, a central axis extending between the first and second ends, a channel at the first end for receiving the rod, and an accommodation space at the second end for pivotably receiving the head;

a pressure element positionable in the receiving part and comprising a rod contacting surface configured to extend into the channel to engage the rod, a head contacting surface to engage and exert pressure on the head, and a flexible portion; and a separate seat configured to hold the head in the receiving part;

wherein when the head, the pressure element, and the seat are in the receiving part, a first surface of the flexible portion of the pressure element is configured to engage a second surface of the receiving part, such that the engagement urges the pressure element axially downwardly to exert pressure on the head; and wherein one of the first or second surfaces extends perpendicularly to the central axis at the engagement while the other one of the first or second surfaces is inclined relative to the central axis at the engagement.

20. The bone anchoring device of claim 19, wherein at least one of the first or second surfaces forms part of a rounded corner that is engageable with the other one of the first or second surfaces.

21. The bone anchoring device of claim 19, wherein the inclined surface extends constantly at a first angle relative to the central axis as the inclined surface extends axially.

22. The bone anchoring device of claim 19, wherein the pressure element is configured to be urged axially downwardly to exert pressure on the head while the channel for the rod remains substantially vacant or unobstructed.

* * * * *